US010827999B2

(12) United States Patent
Matsutani

(10) Patent No.: US 10,827,999 B2
(45) Date of Patent: Nov. 10, 2020

(54) DYNAMIC ANALYSIS APPARATUS AND SYSTEM FOR MEASURING TEMPORAL CHANGES IN BLOOD VESSELS

(71) Applicant: KONICA MINOLTA, INC., Tokyo (JP)

(72) Inventor: Noritsugu Matsutani, Musashino (JP)

(73) Assignee: KONICA MINOLTA, INC., Tokyo (JP)

(*) Notice: Subject to any disclaimer, the term of this patent is extended or adjusted under 35 U.S.C. 154(b) by 135 days.

(21) Appl. No.: 16/137,459

(22) Filed: Sep. 20, 2018

(65) Prior Publication Data
US 2019/0090835 A1 Mar. 28, 2019

(30) Foreign Application Priority Data
Sep. 27, 2017 (JP) ................................. 2017-185574

(51) Int. Cl.
*A61B 6/00* (2006.01)
*G06T 7/00* (2017.01)
*G16H 50/30* (2018.01)

(52) U.S. Cl.
CPC ............ *A61B 6/5217* (2013.01); *A61B 6/486* (2013.01); *A61B 6/504* (2013.01); *A61B 6/507* (2013.01); *G06T 7/0016* (2013.01); *G16H 50/30* (2018.01); *G06T 2207/30061* (2013.01); *G06T 2207/30101* (2013.01)

(58) Field of Classification Search
CPC ....... A61B 6/5217; A61B 6/486; A61B 6/504; A61B 6/507; G06T 7/0016; G06T 2207/30101; G06T 2207/30061; G16H 50/30
See application file for complete search history.

(56) References Cited

U.S. PATENT DOCUMENTS

| 2008/0269592 | A1* | 10/2008 | Kuth ........................ A61B 5/08 600/410 |
| 2015/0245776 | A1* | 9/2015 | Hirohata ................ A61B 6/032 600/504 |
| 2017/0287132 | A1* | 10/2017 | Ertel ........................ G06T 7/11 |

FOREIGN PATENT DOCUMENTS

JP 4404291 B2 1/2010

* cited by examiner

*Primary Examiner* — Casey L Kretzer
(74) *Attorney, Agent, or Firm* — Holtz, Holtz & Volek PC

(57) ABSTRACT

A dynamic analysis apparatus includes: an index value meter that measures, in a plurality of areas in a dynamic image obtained by performing radiography on a region including a blood vessel with respect to a subject, a temporal change of an index value regarding a position and a shape of the blood vessel; an elongation rate calculator that calculates an elongation rate of the blood vessel in each area on the basis of the temporal change of the index value in each area measured by the index value meter; and an elongation rate display that displays a list of the elongation rate in each area calculated by the elongation rate calculator.

10 Claims, 6 Drawing Sheets

DYNAMIC ANALYSIS APPARATUS AND SYSTEM FOR MEASURING TEMPORAL CHANGES IN BLOOD VESSELS

The entire disclosure of Japanese patent Application No. 2017-185574, filed on Sep. 27, 2017, is incorporated herein by reference in its entirety.

BACKGROUND

Technological Field

The present invention relates to a dynamic analysis apparatus and a dynamic analysis system provided with the dynamic analysis apparatus.

Description of the Related Art

For still image capturing and diagnosis of radiation (X-ray) using a conventional film/screen or stimulable phosphor plate, an attempt to apply dynamic image capturing of a diagnostic target region (referred to as target region) using a semiconductor image sensor such as a flat panel detector (FPD) to diagnosis has been made. Specifically, utilizing the responsiveness of a semiconductor image sensor with respect to reading/erasing of image data, a pulse radiation is continuously emitted from a radiation source in accordance with timing of reading/erasing performed by a semiconductor image sensor, and imaging is performed a plurality of times per second, thereby imaging dynamics of a target region. A doctor can observe a series of movements of the target region by sequentially displaying a series of a plurality of images obtained by the capturing.

In pulmonary diagnosis, it is important to observe whether there is a region in which a pulmonary function (ventilation function and pulmonary blood flow function) is weaken. However, it is difficult for a doctor to observe a dynamic image and visually recognize a portion including functional abnormality. In particular, since there are individual differences in respiratory movement of a lung and pulsation of a heart, it is difficult to visually recognize a portion including abnormality of a ventilation function or a pulmonary blood flow function while considering the individual difference.

In view of the above, it has been proposed to provide doctors with, for early diagnosis, diagnosis support information generated by analyzing a dynamic image obtained by dynamic imaging. For example, JP 4404291 B2 discloses a case where a differential image between frames of a respiratory dynamic image is generated, a difference pixel having the largest absolute value for each corresponding pixel in the differential image between frames is obtained, a maximum value image composed of the difference pixel is generated, and the image is displayed in a manner superimposed on an image of a specific respiratory phase. With the use of such a technique, a local position of pulmonary disease can be detected on the basis of a density change of an image related to a respiratory condition.

In the system in which the pulmonary disease is detected on the basis of the density change of the image as disclosed in JP 4404291 B2, an artifact in density change of the image occurs at times due to a movement of a rib, a body motion, and a change in body thickness caused by respiration.

Specifically, a rib moves into and out of a predetermined region of interest (ROI) due to respiration so that an amount of the density change increases, which has been a factor in an erroneously determining a disease region as being in a healthy condition.

SUMMARY

The present invention has been conceived in view of the above-described problem, and an object of the present invention is to provide a dynamic analysis system that analyzes a dynamic image and detects pulmonary disease in which pulmonary disease can be accurately detected without being influenced by a movement of a rib, a body motion, and a change in body thickness.

To achieve the abovementioned object, according to an aspect of the present invention, a dynamic analysis apparatus reflecting one aspect of the present invention comprises: an index value meter that measures, in a plurality of areas in a dynamic image obtained by performing radiography on a region including a blood vessel with respect to a subject, a temporal change of an index value regarding a position and a shape of the blood vessel; an elongation rate calculator that calculates an elongation rate of the blood vessel in each area on the basis of the temporal change of the index value in each area measured by the index value meter; and an elongation rate display that displays a list of the elongation rate in each area calculated by the elongation rate calculator.

BRIEF DESCRIPTION OF THE DRAWINGS

The advantages and features provided by one or more embodiments of the invention will become more fully understood from the detailed description given hereinbelow and the appended drawings which are given by way of illustration only, and thus are not intended as a definition of the limits of the present invention.

DETAILED DESCRIPTION OF EMBODIMENTS

Figure 1:
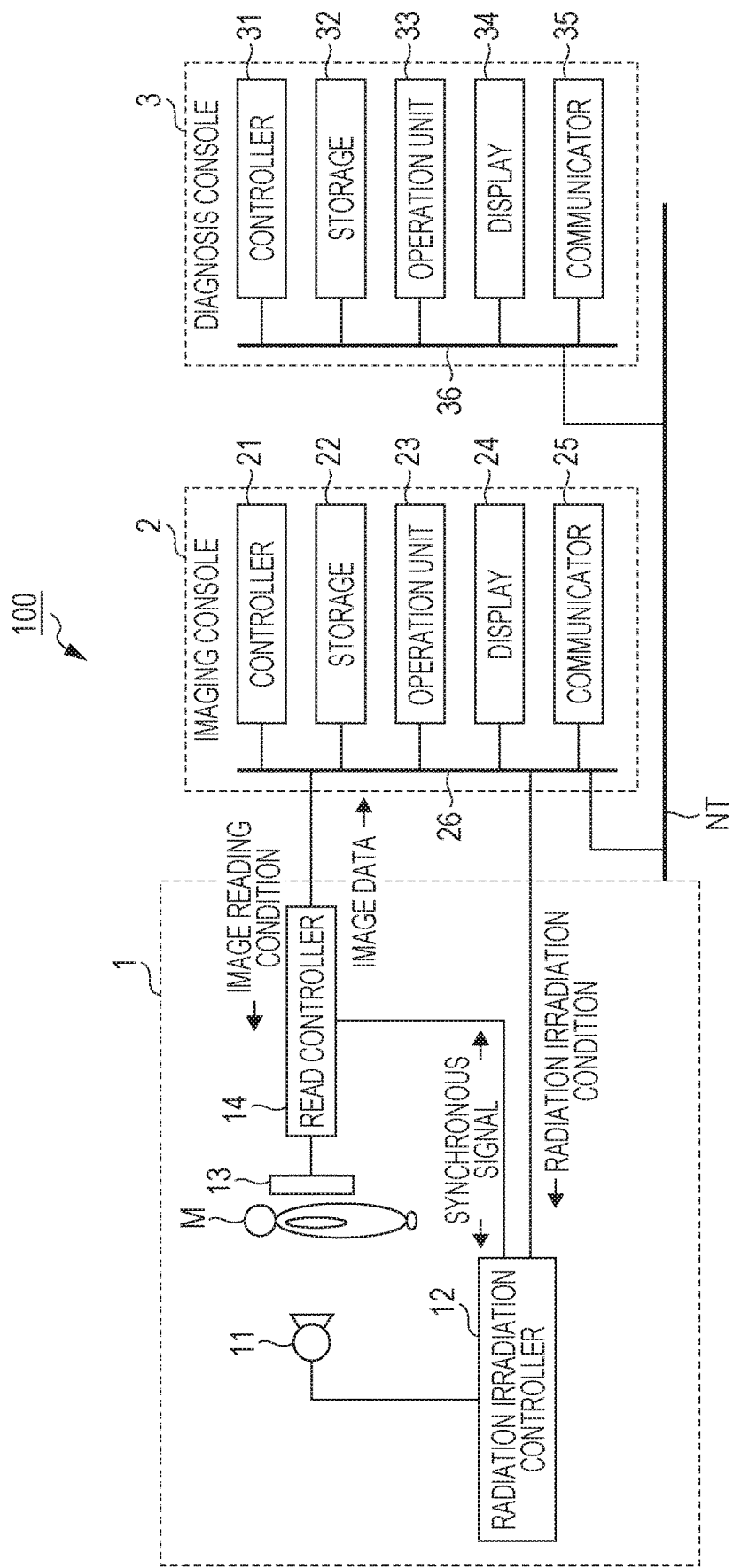
FIG. 1 is a diagram illustrating an overall configuration of a dynamic analysis system according to an embodiment of the present invention.

Hereinafter, an embodiment of the present invention will be described in detail with reference to the drawings. However, the scope of the invention is not limited to the examples illustrated in the drawings.

[Configuration of Dynamic Analysis System 100]

First, a configuration will be described.

FIG. 1 illustrates an overall configuration of a dynamic analysis system 100 according to the present embodiment.

As illustrated in FIG. 1, the dynamic analysis system 100 has a configuration in which an imaging device 1 and an imaging console 2 are connected to each other by a communication cable or the like and the imaging console 2 and a diagnosis console 3 are connected to each other via a communication network NT such as a local area network (LAN). Each device included in the dynamic analysis system 100 conforms to the digital imaging and communications in medicine (DICOM) standard, and communication between the devices is performed in accordance with the DICOM.

The imaging device 1 and the imaging console 2 may be connected to each other via a communication network, and the imaging console 2 and the diagnosis console 3 may be connected to each other by a communication cable.

Further, although the case where the imaging console 2 and the diagnosis console 3 are separately provided is exemplified in FIG. 1, these may be integrally (as one device having fictions of both imaging console and diagnosis console) provided.

[Configuration of Imaging Device 1]

The imaging device 1 is, for example, an imaging means that images dynamics having periodicity (cycle) such as a pulmonary form change of expansion and contraction due to a respiratory movement, and a pulsation of a heart. Dynamic imaging indicates an action that obtains a plurality of images indicating dynamics by repeatedly irradiating a subject with pulse radiation such as an X-ray at a predetermined time interval (pulse irradiation) or continuously irradiating the subject with radiation at a low dose rate (continuous irradiation). A series of images obtained by the dynamic imaging is referred to as a dynamic image. Besides, each of a plurality of images constituting a dynamic image is referred to as a frame image. In the following embodiment, a case where the dynamic imaging is performed by the pulse irradiation will be described as an example.

A radiation source 11 is disposed at a position facing a radiation detector 13 with a subject M interposed therebetween, and irradiates the subject M with radiation (X-ray) under the control of a radiation irradiation controller 12.

The radiation irradiation controller 12 is connected to the imaging console 2, and performs radiography by controlling the radiation source 11 on the basis of a radiation irradiation condition input from the imaging console 2. The radiation irradiation condition input from the imaging console 2 is, for example, a pulse rate, a pulse width, a pulse interval, the number of imaging frames per imaging, a value of an X-ray tube current, a value of an X-ray tube voltage, a type of an additional filter, and the like. The pulse rate is the number of radiation irradiation per second, which coincides with a frame rate to be described later. The pulse width is a radiation irradiation period of time per radiation irradiation. The pulse interval is a period of time from a start of one radiation irradiation to a start of the next radiation irradiation, which coincides with a frame interval to be described later.

The radiation detector 13 includes a semiconductor image sensor such as an FPD. The FPD includes, for example, a glass substrate and the like, and a plurality of detection elements(pixels) is disposed in a matrix at a predetermined position on the substrate. The plurality of detection elements detects the radiation emitted from the radiation source 11 and having passed through at least the subject M according to intensity of the radiation, converts the detected radiation into an electric signal, and accumulates the electric signal. Each pixel includes, for example, a switching part such as a thin film transistor (TFT). The FPD may be an indirect conversion type that converts an X-ray into an electric signal by a photoelectric conversion element via a scintillator or may be a direct conversion type that directly converts an X-ray into an electric signal.

The radiation detector 13 is provided to face the radiation source 11 with the subject M interposed therebetween.

A read controller 14 is connected to the imaging console 2. The read controller 14 controls the switching part included in each pixel of the radiation detector 13 on the basis of an image reading condition input from the imaging console 2, switches the reading of the electric signal accumulated in each pixel, and reads the electric signal accumulated in the radiation detector 13, thereby obtaining image data. This image data is a frame image. Then, the read controller 14 outputs the obtained frame image to the imaging console 2. The image reading condition is, for example, a frame rate, a frame interval, a pixel size, and an image size (matrix size). The frame rate is the number of frame images to be obtained per second, which coincides with the pulse rate. The frame interval is a period of time from a start of operation of obtaining one frame image to a start of operation of obtaining the next frame image, which coincides with the pulse interval.

Here, the radiation irradiation controller 12 and the read controller 14 are connected to each other, and a synchronous signal are mutually exchanged so that the radiation irradiation operation and the image reading operation are synchronized.

[Configuration of Imaging Console 2]

The imaging console 2 controls the radiography and the reading operation of a radiography image performed by the imaging device 1 by outputting the radiation irradiation condition and the image reading condition to the imaging device 1, and displays the dynamic image obtained by the imaging device 1 such that an operator of the radiography such as a radiography engineer confirms the positioning and checks whether the image is suitable for diagnosis.

As illustrated in FIG. 1, the imaging console 2 includes a controller 21, a storage 22, an operation unit 23, a display 24, and a communicator 25, and each unit is connected to one another by a bus 26.

The controller 21 includes a central processing unit (CPU), a random access memory (RAM), and the like. The CPU of the controller 21 reads a system program and various processing programs stored in the storage 22 in accordance with operation of the operation unit 23, expands the read programs in the RAM, and executes, in accordance with the expanded programs, various processing such as imaging control processing to be described later, thereby centrally controls operation of each part of the imaging console 2 and the radiation irradiation operation and the reading operation performed by the imaging device 1.

The storage 22 includes a non-volatile semiconductor memory, a hard disk, or the like. The storage 22 stores various programs to be executed by the controller 21, a parameter necessary for execution of processing based on the program, or data such as a processing result. For example, the storage 22 stores a program for executing an imaging control process illustrated in FIG. 2. Further, the storage 22 stores a radiation irradiation condition and an image reading condition in association with an imaging region. The various programs are stored in the form of readable program codes, and the controller 21 sequentially executes the operation according to the program code.

The operation unit 23 includes a keyboard including a cursor key, a numeral input key, and various function keys, and a pointing device such as a mouse, and outputs an instruction signal input by key operation on the keyboard or mouse operation to the controller 21. Further, the operation unit 23 may include a touch panel on a display screen of the display 24, and in this case, outputs an instruction signal input via the touch panel to the controller 21.

The display 24 includes a monitor such as a liquid crystal display (LCD) and a cathode ray tube (CRT), and displays an input instruction, data, and the like from the operation unit 23 in accordance with an instruction of a display signal input from the controller 21.

The communicator 25 includes a LAN adapter, a modem, a terminal adapter (TA), and the like, and controls data transmission/reception with each device connected to the communication network NT.

[Configuration of Diagnosis Console 3]

The diagnosis console 3 is a dynamic analysis apparatus for supporting diagnosis by a doctor, which obtains a dynamic image from the imaging console 2 and displays the obtained dynamic image and an analysis result of the dynamic image.

As illustrated in FIG. 1, the diagnosis console 3 includes a controller 31, a storage 32, an operation unit 33, a display 34, and a communicator 35, and each unit is connected to one another by a bus 36.

The controller 31 includes a CPU, a RAM, and the like. The CPU of the controller 31 reads a system program and various processing programs stored in the storage 32 in accordance with operation of the operation unit 33, expands the read programs in the RAM, and executes, in accordance with the expanded programs, various processing such as image analysis processing to be described later, thereby centrally controls operation of each part of the diagnosis console 3.

The storage 32 includes a non-volatile semiconductor memory, a hard disk, or the like. The storage 32 stores various programs such as a program for the controller 31 to execute image analysis processing to be described later, a parameter necessary for execution of processing based on the program, or data such as a processing result. These various programs are stored in the form of readable program codes, and the controller 31 sequentially executes the operation according to the program code.

The operation unit 33 includes a keyboard including a cursor key, a numeral input key, and various function keys, and a pointing device such as a mouse, and outputs an instruction signal input by key operation on the keyboard or mouse operation to the controller 31. Further, the operation unit 33 may include a touch panel on a display screen of the display 34, and in this case, outputs an instruction signal input via the touch panel to the controller 31.

The display 34 includes a monitor such as an LCD and a CRT, and performs various displays in accordance with an instruction of a display signal input from the controller 31.

The communicator 35 includes a LAN adapter, a modem, a TA, and the like, and controls data transmission/reception with each device connected to the communication network NT.

[Operation of Dynamic Analysis System 100]

Next, operation of the dynamic analysis system 100 will be described.

(Operation of Imaging Device 1 and Imaging Console 2)

First, imaging operation performed by the imaging device 1 and the imaging console 2 will be described.

Figure 2:
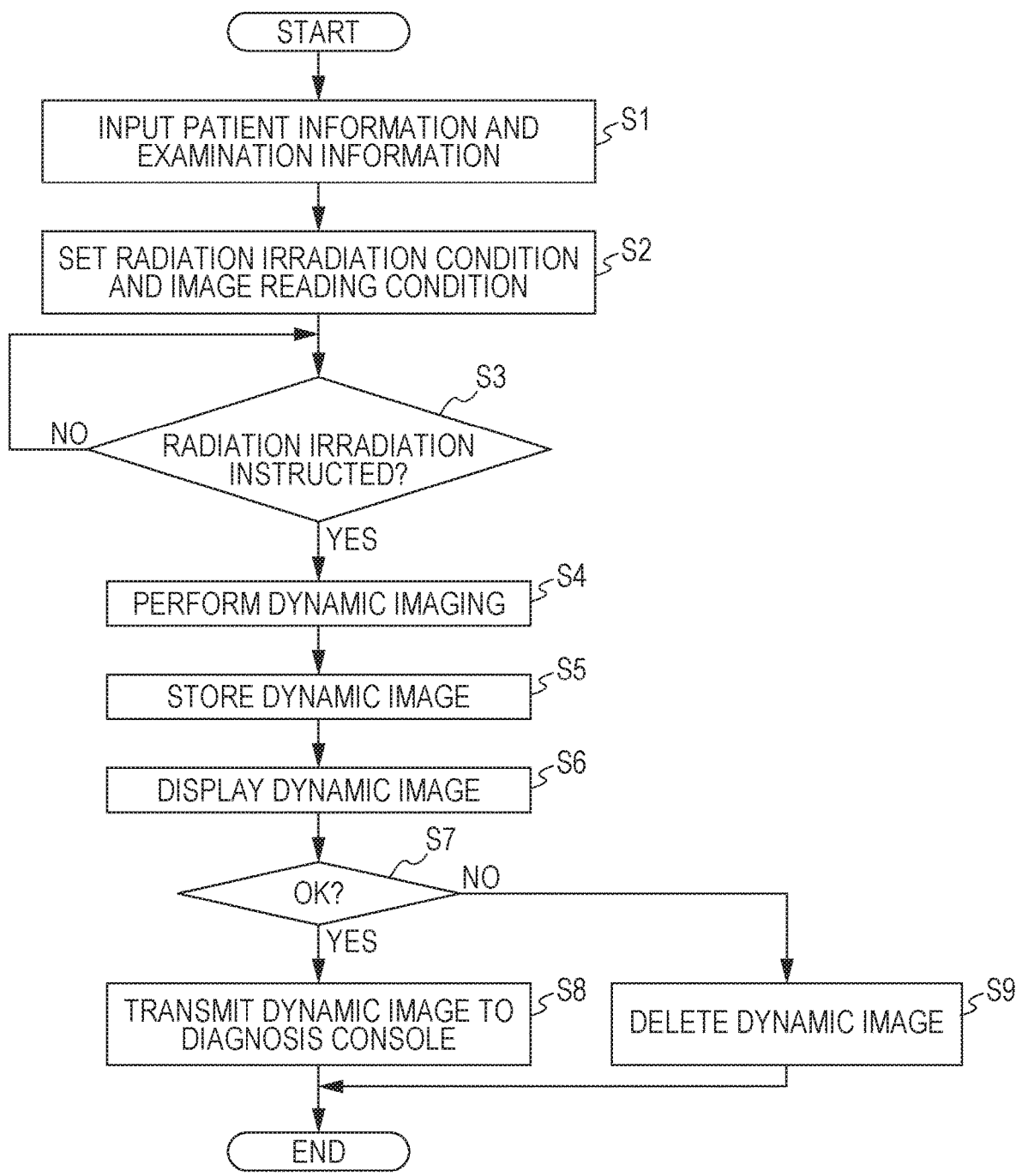
FIG. 2 is a flowchart illustrating an imaging control process executed by an imaging console included in the dynamic analysis system in FIG. 1.

FIG. 2 illustrates an imaging control process executed by the controller 21 of the imaging console 2. The imaging control process is executed in cooperation with the controller 21 and the program stored in the storage 22.

First, the operation unit 23 of the imaging console 2 is operated by a radiography operator, and patient information (name, height, weight, age, gender, etc. of a patient) of a subject (subject M) and examination information (e.g., imaging region (chest region in this case) and method of breathing (deep breathing and quiet breathing)) are input (step S1).

Then, the radiation irradiation condition is read from the storage 22 and set in the radiation irradiation controller 12, and the image reading condition is read from the storage 22 and set in the read controller 14 (step S2).

Subsequently, an instruction on radiation irradiation based on operation of the operation unit 23 is made standby (step S3). Here, the radiography operator places a region of the subject M including a blood vessel (e.g., lung field) between the radiation source 11 and the radiation detector 13, and performs positioning. Further, since the radiography is performed under a breathing condition in the present embodiment, the subject (subject M) is instructed to relax and urged to perform quiet breathing. Alternatively, a guidance on deep breathing such as "take a breath in, and out" may be performed. At the time when the preparation for the radiography is completed, the operation unit 23 is operated to input the instruction on radiation irradiation.

When the instruction on radiation irradiation is input by the operation unit 23 (Yes in step S3), an instruction on an imaging start is output to the radiation irradiation controller 12 and the read controller 14, and the dynamic imaging is started (step S4). That is, radiation is emitted by the radiation source 11 at the pulse interval set in the radiation irradiation controller 12, and a frame image is obtained by the radiation detector 13.

When the imaging of the predetermined number of frames is completed, an instruction on an imaging end is output to the radiation irradiation controller 12 and the read controller 14 by the controller 21, and the imaging operation is stopped. The number of frames to be captured is the number by which at least one breathing cycle can be captured.

The frame images obtained by the radiography are sequentially input to the imaging console 2, stored in the storage 22 in association with the number indicating the imaging order (frame number) (step S5), and displayed on the display 24 (step S6). The radiography operator confirms the positioning and the like using the displayed dynamic image, and determines whether an image suitable for diagnosis has been obtained by the imaging (imaging OK) or re-imaging is necessary (imaging NG). Then, the operation unit 23 is operated to input a determination result.

There may be a case where the frame image is directly output to the diagnosis console 3 without passing through the imaging console 2.

When the determination result indicating imaging OK is input by a predetermined operation of the operation unit 23 (Yes in step S7), an identification ID for identifying the dynamic image and information such as the patient information, the examination information, the radiation irradiation condition, the image reading condition, and the number indicating the imaging order (frame number) are added (e.g., written in a header area of image data in the DICOM format) to each of the series of frame images obtained by the dynamic imaging, and the frame images are transmitted to the diagnosis console 3 via the communicator 25 (step S8). The present process is then terminated. On the other hand, when the determination result indication imaging NG is input by a predetermined operation of the operation unit 23 (No in Step S7), the series of frame images stored in the storage 22 is deleted (step S9), and the present process is terminated. In this case, re-imaging is necessary.

(Operation of Diagnosis Console 3)

Figure 3:
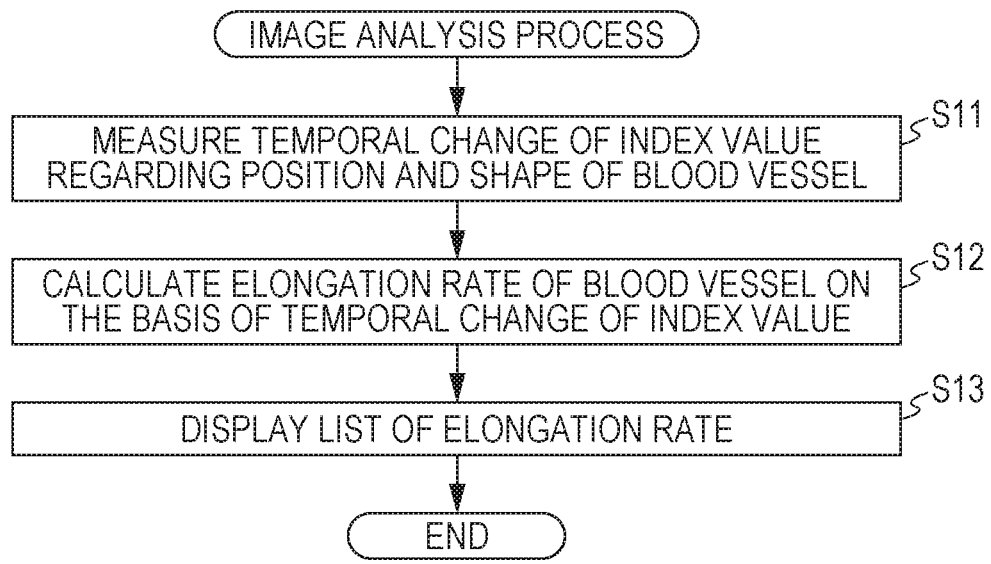
FIG. 3 is a flowchart illustrating an image analysis process executed by a diagnosis console included in the dynamic analysis system in FIG. 1.

Next, operation of the diagnosis console 3 will be described. FIG. 3 is a flowchart illustrating an image analysis process executed by the diagnosis console 3.

The diagnosis console 3 executes the image analysis process illustrated in FIG. 3 in cooperation with the controller 31 and the program stored in the storage 32 in response to the phenomenon in which image data of the series of frame images of the dynamic image has been input from the imaging console 2 via the communicator 35, or a predetermined operation has been performed on the operation unit 33 in a state where the image data of the series of frame images is stored in the storage 32, for example.

In the image analysis process, first, a temporal change of an index value regarding a position and a shape of a blood vessel is measured in a plurality of areas in the input dynamic image (step S11). Specifically, an index value of each area is measured with respect to each of the plurality of frame images included in the dynamic image of the chest region.

As a manner of setting a measurement target region R, for example, a lung field may be divided into a plurality of small regions using a square to set the small region as a measurement target region R, or a circle having a center point set on the image, a polygon having a plurality of vertices, or only a blood vessel region extracted from the lung field using the image analysis may be set as a measurement target region R.

A temporal change of a measured value can be known by arranging the measured value in the measurement target region R corresponding to each frame image in a time series.

In the present embodiment, for example, at least one of the following (1) to (3) is measured as an index value.
(1) Distance between markers
(2) Number of markers
(3) Vascular density A concrete measurement method of these will be described below.

(1) Distance Between Markers

A pulmonary blood vessel repeats expansion and contraction corresponding to pulmonary expansion and contraction. That is, when two or more predetermined portions (points) on a blood vessel are set, the distance between them changes. Accordingly, in (1), a distance between two points set on one pulmonary blood vessel is measured as an index value.

Figure 4A:
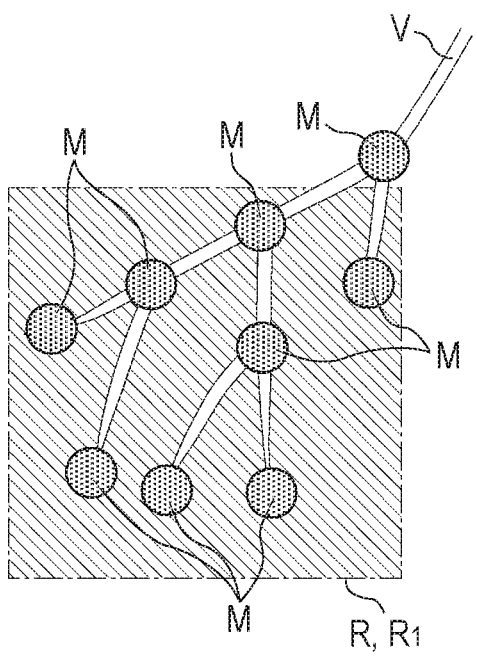
FIGS. 4A and 4B are exemplary arrangements of markers for measuring an index value.

Specifically, first, a plurality of markers M is disposed in a frame image. A method of disposing the marker M is not particularly limited, and the marker M may be disposed, for example, in a randomly distributed manner or in an aligned manner. For example, as illustrated in FIG. 4A, a measurement accuracy can be improved by attaching the marker M to a branch point and a tip of a blood vessel V.

Figure 4B:
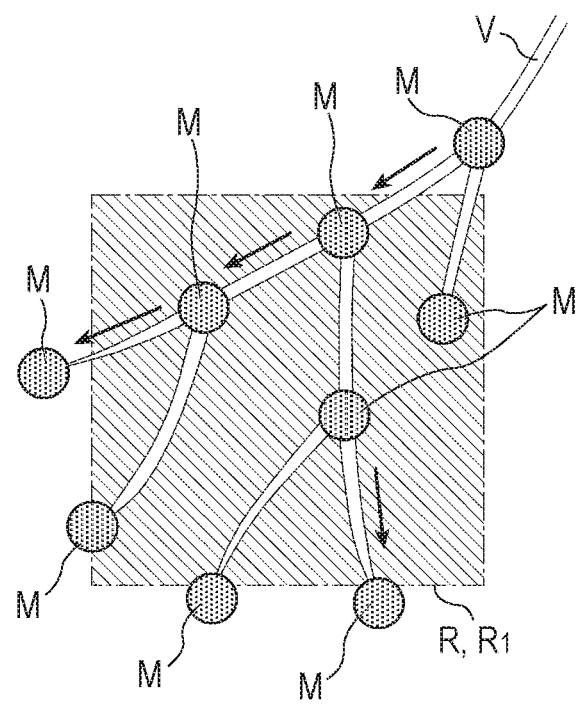

After disposing the marker M in one frame image, the marker M is sequentially disposed in other frame images as well. Since the subject moves and deforms as time goes on, it is necessary to track the portion (point) to which the marker M is attached every time it moves to the next frame image. Tracking of the portion (point) to which the marker M is attached is performed using, for example, a conventional publicly known image processing technique such as a pattern matching (method of holding an image of the blood vessel V in the vicinity of the marker M and locating a matching area in an image after a deformation) and an optical flow (indicating a movement of a portion with a vector). Accordingly, the marker M can be attached to the same portion even when the position or the shape of the subject is different for each frame image. That is, as illustrated in FIG. 4B, the marker M moves corresponding to the pulmonary expansion and contraction (movement of the portion).

Since a tissue around the blood vessel V expands and contracts along with the pulmonary blood vessel V, the change in distance with respect to the marker M disposed around the blood vessel V can be regarded as the expansion contraction of the blood vessel V.

Figure 5A:
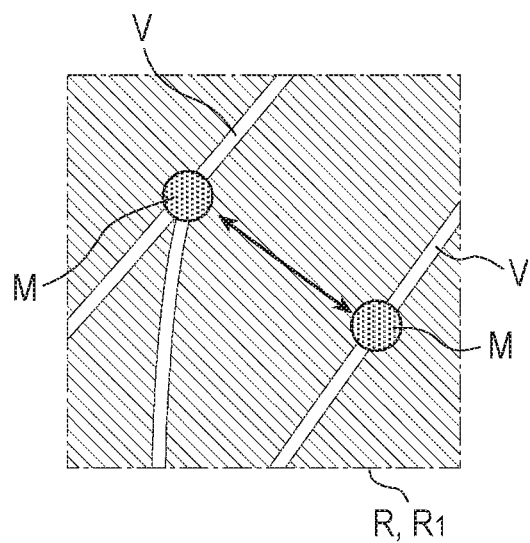
FIGS. 5A and 5B are exemplary arrangements of markers for measuring the index value.

Accordingly, as illustrated in FIG. 5A, a distance between two points respectively set on two different blood vessels V may be measured as an index value.

Figure 5B:
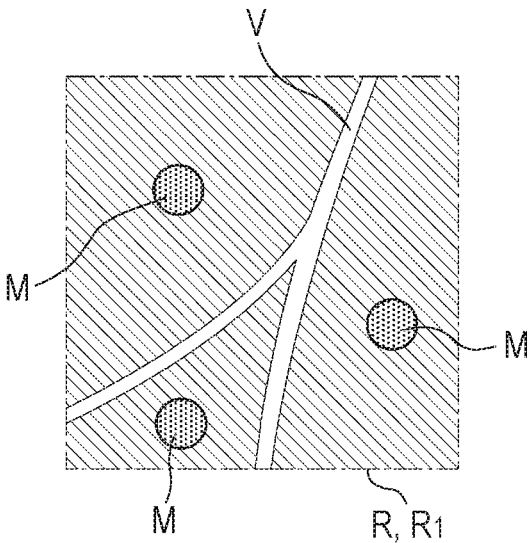

Further, as illustrated in FIG. 5B, a plurality of markers M may be disposed around the blood vessel V to measure the distance between them, or an area of a polygon formed by connecting three or more adjacent markers M with a straight line may be measured.

Furthermore, a distance between the marker M disposed on the blood vessel V and the marker M disposed around the blood vessel V or an area of a figure based on them may be measured.

After the marker M is attached, the distance between the predetermined two markers M is measured for each frame image. It may be a distance between adjacent markers M or a distance between distanced markers M. It may be an average value of several measured values.

(2) Number of Markers

When a plurality of markers M is disposed to be distributed throughout the lung field, the plurality of markers M repeats separating and gathering corresponding to pulmonary expansion and contraction. That is, when an area that does not moves and deforms is set in the lung field, the markers M in the area repeatedly move into and out of the area so that the number of markers within the area increases and decreases. Accordingly, in (2), the number of markers within the area is measured as an index value.

Specifically, first, a plurality of markers M is attached within the area in each frame image. Similar to (1), a method of attaching the marker M is not particularly limited.

Then, at least one small region R1 is set in the lung field. The small region R1 may be the same as the measurement target region R described above, or may be further set therein. A size and coordinates of the small region R1 are matched in each frame image.

After attaching the marker M and setting the small region R1, the number of markers within the small region R1 in each frame image is counted.

Here, a specific marker M may be selected from the small region R1, and the number of the markers M, which are within a circle having the specific marker M as a center point or within a polygonal closed area having the specific marker M as a center or as a vertex, may be measured.

(3) Vascular Density

When a lung expands, a distance between adjacent blood vessels may increase. That is, when an area that does not moves and deforms is set in the lung field, the density of the blood vessel occupying the area increases and decreases. Accordingly, in (3), the density of the pulmonary, blood vessel region occupying the area is measured as an index value. In the present embodiment, an area (occupancy rate (%)) of the blood vessel region occupying a predetermined area or the number of blood vessels existing within the predetermined area is measured as a more specific value of the density.

(3-1) Blood Vessel Region Occupancy Rate

Figure 6:
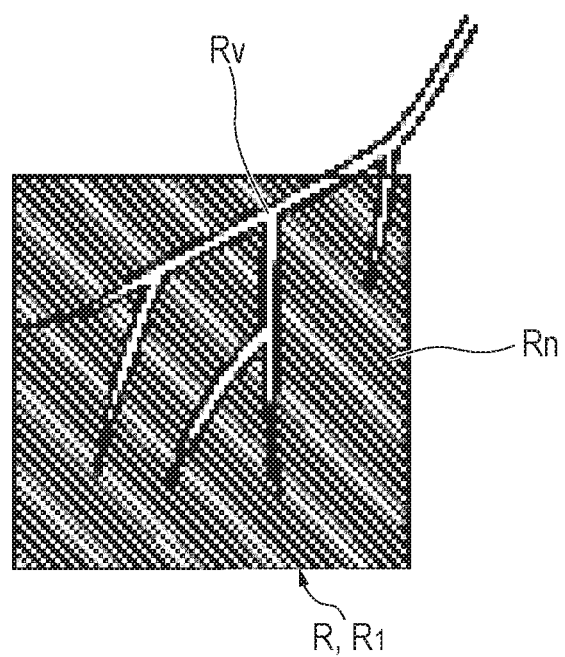
FIG. 6 is exemplary processing of an image for measuring the index value.

First, a blood vessel is detected by applying predetermined image processing to a dynamic image. Specifically, a threshold value is set between a signal value of a pixel of the blood vessel and a signal value of a tissue other than the blood vessel, and a frame image is binarized. Accordingly, as illustrated in FIG. 6, the frame image is divided into a blood vessel region Rv in which the blood vessel V is drawn and a non-blood vessel region Rn other than the blood vessel region. That is, the diagnosis console 3 functions as a blood vessel detector in the present invention.

When the binarizing processing is performed, it is preferable to determine a region of a bone such as a rib in advance and perform calculation while the bone region is excluded.

After detecting the blood vessel V, at least one small region R1 is set in the lung in each frame image. A method of setting the small region R1 is similar to (2).

After setting the small region R1, an area (occupancy rate) of the blood vessel region Rv occupying the small region R1 in each frame image is calculated.

Here, a specific marker M may be selected from the small region R1, and an occupancy rate of the blood vessel region Rv in a circular or polygonal closed area obtained by connecting each marker M with a line may be measured.

(3-2) Number of Blood Vessel

First, a plurality of markers M is disposed on the blood vessel V, and a line connecting adjacent markers M is defined as a blood vessel model. Then, at least one small region R1 is set in the lung in each frame image. The method of setting the small region R1 is similar to (2) and (3).

Subsequently, the number of the blood vessels V existing within the small region R1 in each frame image is counted.

The above-described diagnosis console 3 according to the present embodiment, which measures the temporal change of various index values, serves as an index value meter in the present invention.

After measuring the temporal change of the index value regarding the position and the shape of the blood vessel V, an elongation rate of the blood vessel V in each measurement target region R is calculated on the basis of the temporal change of the index value in each measurement target region R (step S12). In the present embodiment, the elongation rate is calculated on the basis of at least one of a difference between index values at two time points, an increase rate of the index value, an acceleration level of the index value, and an increase start timing of the index value.

Figure 7A:
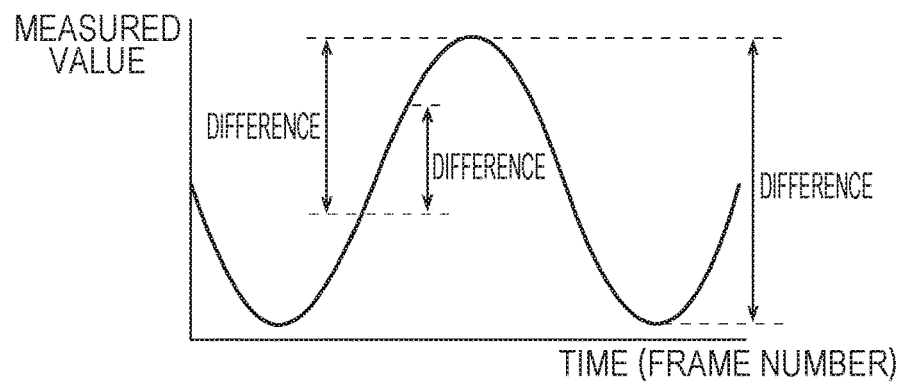
FIGS. 7A to 7D are examples of a temporal change of the index value to be measured.

As illustrated in FIG. 7A, the difference between the index values is a difference between a measured value (maximum value, minimum value, or intermediate value) at a predetermined time point and a measured value (maximum value, minimum value, or intermediate value) at a time point later than the predetermined time point when a plurality of obtained measured values is made into a graph with a horizontal axis representing time (frame number) and a vertical axis representing a measured value. A ratio of them may be used.

Figure 7B:
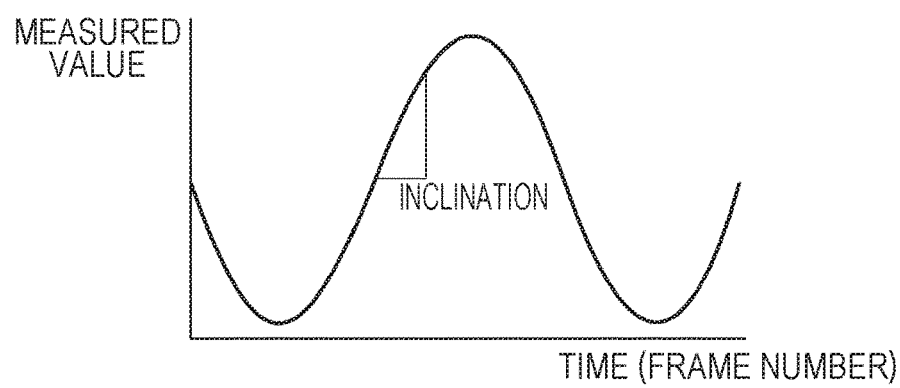

As illustrated in FIG. 7B, the increase rate is an increase amount (inclination of the graph) of the measured value per unit time in a period in which the measured value increases.

Figure 7C:
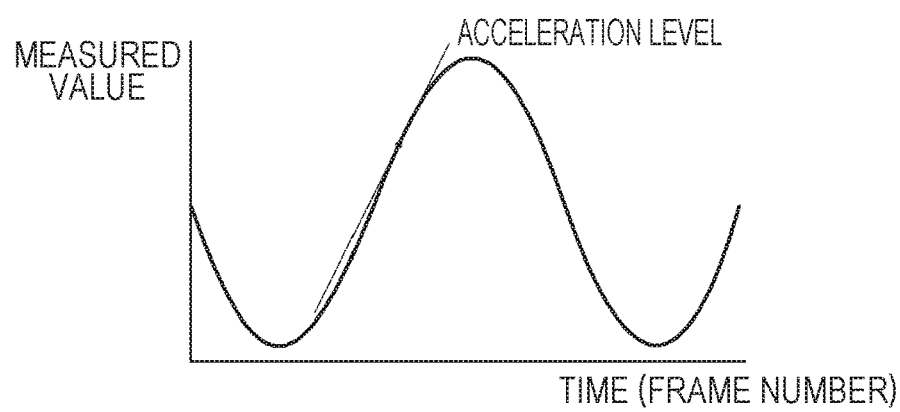

As illustrated in FIG. 7C, the acceleration level is an increase amount (inclination of a tangent of the graph) of the measured value at a certain time point when the measured value is increasing.

Figure 7D:
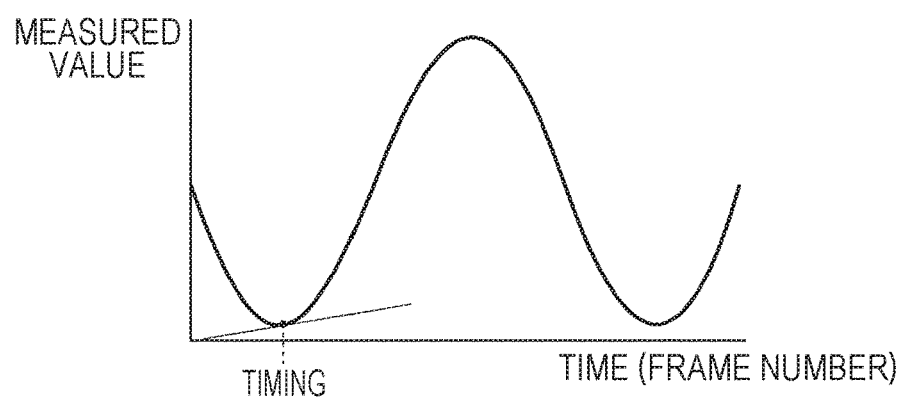

As illustrated in FIG. 7D, the increase start timing is a timing at which the increase starts (inclination of the tangent of the graph becomes equal to or more than a predetermined value).

When the marker M is used for measuring the index value, the obtained measured value is stored on the marker M and mapped on the dynamic image using character/color information.

On the other hand, when the marker M is not used for measuring the index value, the measured value is stored for each measured position (coordinates) and mapped on the dynamic image using character/color information.

The above-described diagnosis console 3 according to the present embodiment, which calculates the elongation rate, serves as an elongation rate calculator in the present invention.

After calculating the elongation rate, the calculated elongation rate in each region is displayed in a list (step S13). As a manner of displaying the list, it may be in a form of a table, or it may be displayed at a position corresponding to the image (that may be a still image or a dynamic image) of the imaging region.

Figure 8A:
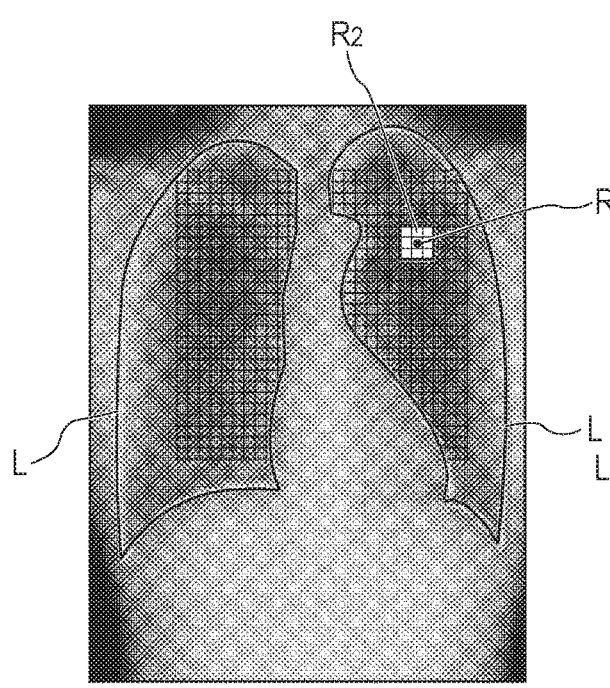
FIGS. 8A and 8B are schematic diagrams illustrating a method of comparing elongation amounts.
Figure 8B:
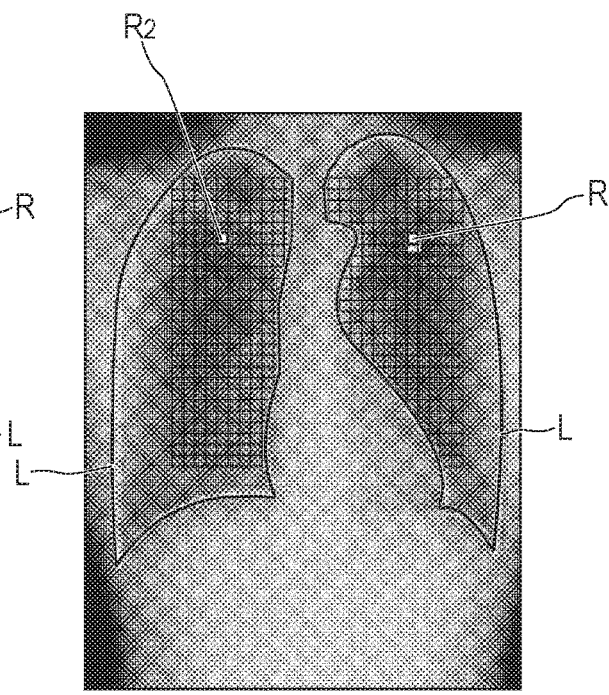

A user checks the list display and compares the elongation rate in a certain measurement target region R with the elongation rate in another region R2. Specifically, as illustrated in FIG. 8A, the elongation rate in the region R2 around the measurement target region R is compared. Alternatively, as illustrated in FIG. 8B, the elongation rate in a certain measurement target region R in a lung L on one of the left/right side is compared with the elongation rate in the corresponding (at a bilaterally symmetrical position) region R2 in a lung L on the other side.

Since it is unlikely that the elongation rate in a specific region significantly differs from the surroundings in a healthy (disease-free) lung, in a case where the elongation rate in a certain measurement target region R significantly differs (small or slow) from the elongation rate of the surrounding region, it is highly likely that there is an abnormality such as a disease in the region corresponding to the measurement target region R in the lung field.

The above-described diagnosis console 3 that displays a list of the elongation rate servers as an elongation rate display in the present invention.

Here, instead of being compared with the elongation rate in another region, a predetermined reference value may be held in advance and compared with the reference value.

Figure 9:
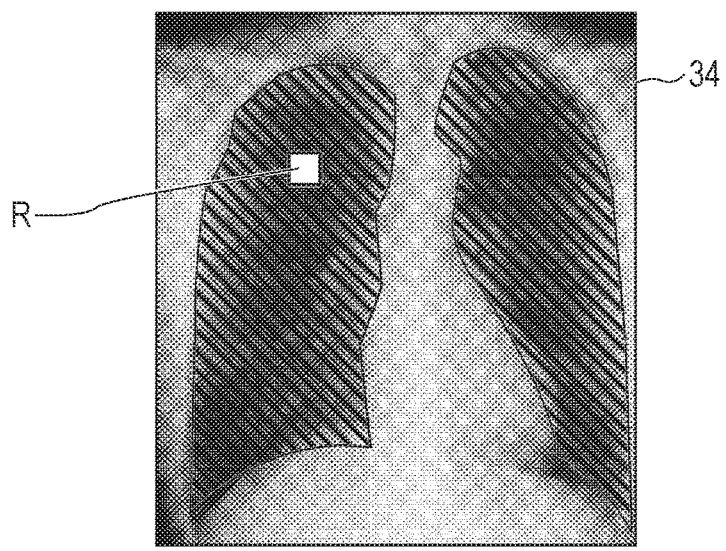
FIG. 9 is an exemplary list display of the elongation amount.

Further, as illustrated in FIG. 9, the diagnosis console 3 according to the present embodiment is capable of displaying, on the display 34, a still image (color mapping) of the imaging region in which a color corresponding to the elongation rate is applied to each region. By setting the measurement target region R having a relatively low elongation rate to a color different from the surroundings (white in this case), it becomes easier to find a region in which the elongation rate significantly differs from others than to directly display the numerical values in the list.

At that time, the numerical value of the elongation rate may be displayed together with the display by color. The elongation rates in all the small region R1 may be constantly displayed in the list, or the elongation rates only in the region specified (clicked or matched with a cursor) by the operation unit 33 on the color mapping display image may be displayed.

As described above, the diagnosis console 3 includes an input unit that inputs image data of the dynamic image obtained by performing the radiography on the lung field (portion including the blood vessel V) of the subject, the index value meter that measures the temporal change of the index value regarding the position and the shape of the pulmonary blood vessel V in the plurality of measurement target regions R in the dynamic image input by the input unit, the elongation rate calculator that calculates the elongation rate of the pulmonary blood vessel V in each measurement target region R on the basis of the temporal change of the index value in each measurement target region R measured by the index value meter, and the elongation rate display that displays a list of the elongation rate in each measurement target region R calculated by the elongation rate calculator.

Accordingly, the diagnosis console 3 can detect a hard region in the lung field without using the change in density of the image, whereby pulmonary disease can be accurately detected without being influenced by a movement of a rib, a body motion, and a change in body thickness.

Note that the description of the present embodiment is an example of the dynamic analysis system according to the present invention, and is not limited thereto.

For example, although the exemplary case where the softness of the lung or the pulmonary blood vessel V is evaluated as a target region from the chest region dynamic image obtained by imaging dynamics of the chest region of the human body has been described in the embodiment above, it is not limited thereto, and may be applied to a case where the softness of another region is evaluated from the dynamic image obtained by imaging another region.

Further, for example, although the exemplary case where the hard disk, the non-volatile semiconductor memory, or the like is used as a computer readable medium of the program according to the present invention has been disclosed, it is not limited to this example. A portable recording medium such as a CD-ROM may be applied as another computer readable medium. Furthermore, a carrier wave (carrier) may also be applied as a medium for providing, via a communication line, data of the program according to the present invention.

Besides, details of the configuration and detailed operation of each device included in the dynamic analysis system 100 may be changed as necessary without departing from the gist of the present invention.

Although embodiments of the present invention have been described and illustrated in detail, the disclosed embodiments are made for purposes of illustration and example only and not limitation. The scope of the present invention should be interpreted by terms of the appended claims.

What is claimed is:

1. A dynamic analysis apparatus, comprising:
an index value meter that measures, in a plurality of areas in a dynamic image obtained by performing radiography on a region including a blood vessel with respect to a subject, a temporal change of an index value regarding a position and a shape of the blood vessel;
an elongation rate calculator that calculates an elongation rate of the blood vessel in each area based on the temporal change of the index value in each area measured by the index value meter; and
an elongation rate display that displays a list of the elongation rate in each area calculated by the elongation rate calculator;
wherein the region including a blood vessel is a lung field; and
wherein the index value meter measures, from among a plurality of points set to be distributed throughout the lung field, a number of the points that are within an area having a fixed size and fixed coordinates that is set in the lung field, as the index value.

2. The dynamic analysis apparatus according to claim 1, further comprising:
a blood vessel detector that detects a pulmonary blood vessel in the lung field by applying predetermined image processing to the dynamic image,
wherein the index value meter further measures a distance between two points set on one pulmonary blood vessel as the index value.

3. The dynamic analysis apparatus according to claim 1, further comprising:
a blood vessel detector that detects a pulmonary blood vessel in the lung field by applying predetermined image processing to the dynamic image,
wherein the index value meter further measures a distance between two points respectively set on two different pulmonary blood vessels as the index value.

4. The dynamic analysis apparatus according to claim 1, further comprising:
a blood vessel detector that detects a pulmonary blood vessel in the lung field by applying predetermined image processing to the dynamic image,
wherein the index value meter further measures an area of a polygon formed by connecting three or more points set around the pulmonary blood vessel with a straight line as the index value.

5. The dynamic analysis apparatus according to claim 1, further comprising:
a blood vessel detector that detects a pulmonary blood vessel in the lung field by applying predetermined image processing to the dynamic image,
wherein the index value meter further measures a density of a pulmonary blood vessel area occupying the area as the index value.

6. The dynamic analysis apparatus according to claim 1, wherein the elongation rate calculator calculates the elongation rate based on any one of a difference between index values at two time points, an increase rate of the index value, an acceleration level of the index value, and an increase start timing of the index value.

7. The dynamic analysis apparatus according to claim 1, wherein the elongation rate display is capable of displaying an image of an imaging region in which a color corresponding to the elongation rate is applied to each area.

8. A dynamic analysis system, comprising:
the dynamic analysis apparatus according to claim 1; and
an imaging device that generates a dynamic image by performing radiography on a region including a blood vessel with respect to a subject and outputs the dynamic image to the dynamic analysis apparatus.

9. A dynamic analysis apparatus, comprising:
an index value meter that measures, in a plurality of areas in a dynamic image obtained by performing radiography on a region including a blood vessel with respect to a subject, a temporal change of an index value regarding a position and a shape of the blood vessel;
an elongation rate calculator that calculates an elongation rate of the blood vessel in each area based on the temporal change of the index value in each area measured by the index value meter; and
an elongation rate display that displays a list of the elongation rate in each area calculated by the elongation rate calculator,
wherein the region including a blood vessel is a lung field,
wherein the dynamic analysis apparatus further comprises a blood vessel detector that detects a pulmonary blood vessel in the lung field by applying predetermined image processing to the dynamic image, and wherein the index value meter measures an area of a polygon formed by connecting three or more points set around the pulmonary blood vessel with a straight line as the index value.

10. A dynamic analysis apparatus, comprising:

an index value meter that measures, in a plurality of areas in a dynamic image obtained by performing radiography on a region including a blood vessel with respect to a subject, a temporal change of an index value regarding a position and a shape of the blood vessel;

an elongation rate calculator that calculates an elongation rate of the blood vessel in each area based on the temporal change of the index value in each area measured by the index value meter; and an elongation rate display that displays a list of the elongation rate in each area calculated by the elongation rate calculator, wherein the region including a blood vessel is a lung field, wherein the dynamic analysis apparatus further comprises a blood vessel detector that detects a pulmonary blood vessel in the lung field by applying predetermined image processing to the dynamic image, wherein the index value meter measures a density of a pulmonary blood vessel area occupying the area as the index value.

* * * * *